United States Patent
Nakasone et al.

(10) Patent No.: US 11,378,542 B2
(45) Date of Patent: Jul. 5, 2022

(54) GAS SENSOR

(71) Applicant: NGK INSULATORS, LTD., Aichi (JP)

(72) Inventors: Osamu Nakasone, Inabe (JP); Taku Okamoto, Nagoya (JP); Nobukazu Ikoma, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 234 days.

(21) Appl. No.: 16/452,714

(22) Filed: Jun. 26, 2019

(65) Prior Publication Data

US 2020/0003724 A1 Jan. 2, 2020

(30) Foreign Application Priority Data

Jun. 27, 2018 (JP) .............................. JP2018-121567

(51) Int. Cl.
*G01N 27/407* (2006.01)
*G01N 27/41* (2006.01)
*G01N 33/00* (2006.01)

(52) U.S. Cl.
CPC ......... *G01N 27/4071* (2013.01); *G01N 27/41* (2013.01); *G01N 33/0037* (2013.01); *G01N 33/0054* (2013.01)

(58) Field of Classification Search
CPC ........... G01N 27/4071; G01N 33/0054; G01N 33/0037; G01N 27/4074; G01N 27/4072; G01N 27/406–41; G01N 33/0004–0075
See application file for complete search history.

(56) References Cited

U.S. PATENT DOCUMENTS

| | | | | | |
|---|---|---|---|---|---|
| 4,777,922 | A | * | 10/1988 | Mieno | F02D 41/1494 123/688 |
| 5,249,453 | A | * | 10/1993 | Usami | G01N 27/4065 204/408 |
| 5,866,799 | A | * | 2/1999 | Kato | G01N 27/419 73/31.05 |

(Continued)

FOREIGN PATENT DOCUMENTS

JP 2009-244048 A 10/2009

OTHER PUBLICATIONS

Von Johannes Brettschneider, "Berechnung des Luftverhältnisses λ von Luft-Kaftstoff-Gemischen und des Einflusses von Meßfehlem auf λ", Bosh Techn. Berichte 6 (1979) 4, pp. 177-186.

*Primary Examiner* — Joshua L Allen
(74) *Attorney, Agent, or Firm* — Mattingly & Malur, PC

(57) ABSTRACT

A gas sensor detects the concentration of a specific gas on the basis of a pump current that flows when oxygen is pumped out from a measurement chamber, so that an oxygen concentration in the measurement chamber becomes a predetermined low concentration, the oxygen that is pumped out being oxygen that is generated when the specific gas is reduced in measurement chamber in a case where the specific gas is an oxide or being oxygen that is generated when a gas obtained as a result of conversion of the specific gas to an oxide is reduced in the measurement chamber in a case where the specific gas is a non-oxide. Further, the gas sensor corrects the pump current or the concentration of the specific gas on the basis of the oxygen concentration of the measurement-object gas when the measurement-object gas is in a rich atmosphere.

6 Claims, 10 Drawing Sheets

(56) References Cited

U.S. PATENT DOCUMENTS

| | | | | |
|---|---|---|---|---|
| 6,635,161 B2* | 10/2003 | Inagaki | ............. | G01N 27/4065 |
| | | | | 204/406 |
| 2008/0237064 A1* | 10/2008 | Nakasone | ............ | G01N 27/419 |
| | | | | 205/781 |
| 2009/0242427 A1* | 10/2009 | Muroguchi | .......... | G01N 27/419 |
| | | | | 205/781 |
| 2014/0332378 A1* | 11/2014 | Nakasone | .......... | G01N 33/0047 |
| | | | | 204/410 |
| 2014/0332379 A1* | 11/2014 | Nakasone | ............. | G01N 27/41 |
| | | | | 204/410 |
| 2015/0034484 A1* | 2/2015 | Nakasone | .......... | G01N 27/4162 |
| | | | | 204/412 |

* cited by examiner

GAS SENSOR

CROSS-REFERENCE TO RELATED APPLICATION

The present application claims priority from Japanese Patent Application No. 2018-121567, filed on Jun. 27, 2018, the entire contents of which are incorporated herein by reference.

BACKGROUND OF THE INVENTION

1. Field of the Invention

The present invention relates to a gas sensor.

2. Description of the Related Art

Currently, various measuring devices are used to determine the concentration of a specific gas component in a measurement-object gas. For example, as a device for measuring the NOx concentration of a measurement-object gas, such as a combustion gas, a gas sensor in which an electrode is formed on a layer of an oxygen-ion-conductive solid electrolyte, such as zirconia ($ZrO_2$), is known (see PTL 1). In such a gas sensor, the concentration of NOx components is measured by detecting, for example, a current that flows through an electrode (measurement electrode) inside a sensor element dependently on the concentration of NOx components as a sensor output.

CITATION LIST

Patent Literature

PTL 1: JP 2009-244048 A

SUMMARY OF THE INVENTION

Meanwhile, the use of a gas in a rich atmosphere containing an unburned fuel as a measurement-object gas has not been studied to date. This time, the present inventors have measured a specific gas component contained in a measurement-object gas in a rich atmosphere and found that accurate measurement is difficult.

The present invention has been made to solve the problem described above, and a major object thereof is to increase the accuracy of measuring a specific gas component contained in a measurement-object gas in a rich atmosphere.

A gas sensor according to the present invention includes:
a layered body that has a plurality of stacked layers of an oxygen-ion-conductive solid electrolyte and in which a measurement-object gas flowing portion that allows a measurement-object gas containing a specific gas to be introduced thereinto and to flow therethrough is provided;
a measurement electrode that is disposed in at least a part of an internal surrounding surface of a measurement chamber in the measurement-object gas flowing portion;
a specific-gas concentration detector that detects a concentration of the specific gas on the basis of a measurement pump current that flows when oxygen is pumped out from the measurement chamber so that an oxygen concentration in the measurement chamber becomes a predetermined low concentration, the oxygen that is pumped out being oxygen that is generated when the specific gas is reduced in the measurement chamber in a case where the specific gas is an oxide or being oxygen that is generated when a gas obtained as a result of conversion of the specific gas to an oxide is reduced in the measurement chamber in a case where the specific gas is a non-oxide; and a corrector that corrects the measurement pump current or the concentration of the specific gas on the basis of an oxygen concentration of the measurement-object gas when the measurement-object gas is in a rich atmosphere.

This gas sensor detects the concentration of the specific gas on the basis of the measurement pump current that flows when oxygen is pumped out from the measurement chamber so that the oxygen concentration in the measurement chamber becomes a predetermined low concentration, the oxygen that is pumped out being oxygen that is generated when the specific gas is reduced in the measurement chamber in a case where the specific gas, which is contained in the measurement-object gas, is an oxide or being oxygen that is generated when a gas obtained as a result of conversion of the specific gas to an oxide is reduced in the measurement chamber in a case where the specific gas, which is contained in the measurement-object gas, is a non-oxide. Further, the gas sensor corrects the measurement pump current or the concentration of the specific gas on the basis of the oxygen concentration of the measurement-object gas when the measurement-object gas is in a rich atmosphere. Here, when the measurement-object gas is in a rich atmosphere, even if the actual concentration of the specific gas contained in the measurement-object gas remains the same, the measurement pump current changes in accordance with the oxygen concentration of the measurement-object gas, and therefore, the detected concentration of the specific gas also changes. That is, the accuracy of measurement of the specific gas component decreases. This has been newly found by the present inventors this time. Accordingly, when the measurement-object gas is in a rich atmosphere, the measurement pump current or the concentration of the specific gas is corrected on the basis of the oxygen concentration of the measurement-object gas. As a consequence, the accuracy of measurement of the specific gas component contained in the measurement-object gas in a rich atmosphere increases.

The gas sensor according to the present invention may further include: an oxygen concentration regulating chamber that is provided on an upstream side of the measurement electrode in the measurement-object gas flowing portion; and an oxygen concentration detector that detects the oxygen concentration of the measurement-object gas on the basis of a regulating pump current that flows when oxygen is pumped out from or pumped into the oxygen concentration regulating chamber so that an oxygen concentration in the oxygen concentration regulating chamber matches a target concentration, in which the corrector may use the oxygen concentration of the measurement-object gas detected by the oxygen concentration detector to make a correction. Accordingly, the gas sensor of the present invention can detect the oxygen concentration of the measurement-object gas. Therefore, the number of sensors can be made smaller than that in a case where the gas sensor of the present invention receives a detection signal of the oxygen concentration detected by a sensor other than the gas sensor of the present invention.

In the gas sensor according to the present invention, the measurement-object gas may be an exhaust gas from an internal combustion engine, and as the oxygen concentration of the measurement-object gas, an air-fuel ratio of the measurement-object gas may be used. The air-fuel ratio of the measurement-object gas can be converted from the oxygen concentration, and therefore, the air-fuel ratio can be used as the oxygen concentration. For example, in a case where the air-fuel ratio of the measurement-object gas is smaller than a stoichiometric air-fuel ratio, that is, the measurement-object gas is in a rich atmosphere, the measurement-object gas contains an unburned gas component. Therefore, the oxygen concentration can be calculated from the amount of oxygen necessary to just sufficiently oxidize the gas component so as to match a target oxygen concentration. In this case, the oxygen concentration is expressed by a minus value.

The gas sensor according to the present invention may further include a storage unit that stores a correspondence between the oxygen concentration of the measurement-object gas and a relative sensitivity of the measurement pump current or a correspondence between the oxygen concentration of the measurement-object gas and a relative sensitivity of the concentration of the specific gas when the measurement-object gas is in a rich atmosphere, in which the corrector may use the correspondence stored in the storage unit to make a correction. Accordingly, the correction can be made relatively easily. Note that the relative sensitivity of the measurement pump current is the ratio of the measurement pump current in a rich atmosphere relative to the measurement pump current in a state where the measurement-object gas has the stoichiometric air-fuel ratio (the oxygen concentration is zero) or in a lean atmosphere. The relative sensitivity of the concentration of the specific gas is the ratio of the concentration of the specific gas in a rich atmosphere relative to the concentration of the specific gas in the state where the measurement-object gas has the stoichiometric air-fuel ratio (the oxygen concentration is zero) or in a lean atmosphere.

The gas sensor according to the present invention may further include a storage unit that stores a correspondence between an actual concentration of the specific gas contained in the measurement-object gas, the oxygen concentration of the measurement-object gas, and the measurement pump current when the measurement-object gas is in a rich atmosphere, in which the corrector may use the correspondence stored in the storage unit to make a correction. Accordingly, the correction can be made with a higher accuracy.

Here, when the actual concentration of the specific gas contained in the measurement-object gas is represented by c [volume ppm], the air-fuel ratio, which is a kind of the oxygen concentration of the measurement-object gas, is represented by R, and the measurement pump current is represented by Ip2 [μA], the correspondence may be expressed by $Ip2=(p^*c+q)^*R+(r^*c+s)$, where p, q, r, and s are constants used when c is within a predetermined low concentration range, or $Ip2=(t^*c+u)^*R+(v^*c+w)$, where t, u, v, and w are constants used when c exceeds the predetermined low concentration range. These expressions are based on the following new findings obtained by the present inventors this time. In a case where, for example, the specific gas is NOx or ammonia, when the actual concentration of the specific gas is kept constant, the measurement pump current linearly changes relative to the oxygen concentration of the measurement-object gas. That is, the measurement pump current is approximated by a linear function of the oxygen concentration. The slope and the intercept of this linear function differ depending on the actual concentration of the specific gas. In a case where the actual concentration of the specific gas is within the low concentration range, the slope is approximated by a linear function of the actual concentration, and the intercept is also approximated by a linear function of the actual concentration. In a case where the actual concentration of the specific gas exceeds the low concentration range, the slope is approximated by a linear function of the actual concentration (a function different from that in the case where the actual concentration of the specific gas is within the low concentration range), and the intercept is also approximated by a linear function of the actual concentration (a function different from that in the case where the actual concentration of the specific gas is within the low concentration range).

DETAILED DESCRIPTION OF THE INVENTION

First Embodiment

Figure 1:
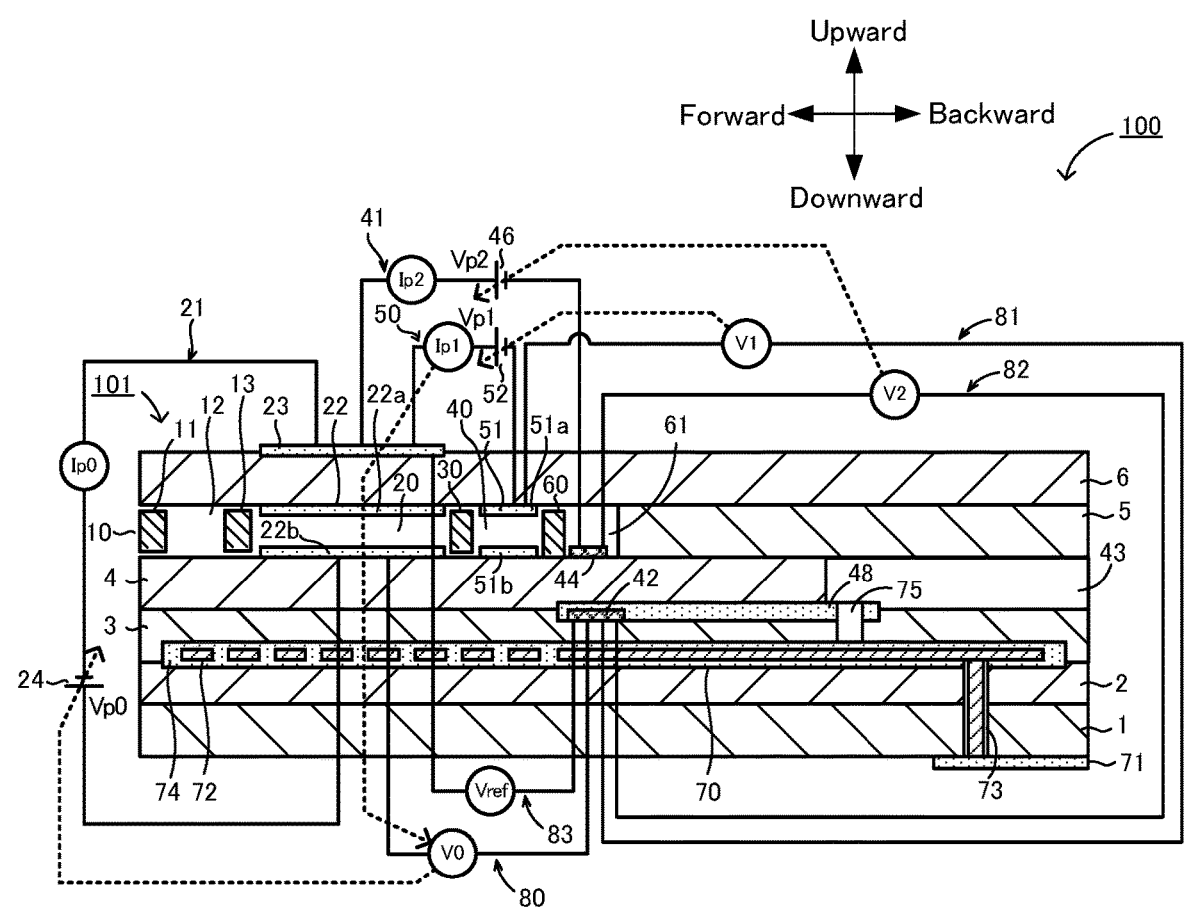
FIG. 1 is a schematic cross-sectional view of a gas sensor 100 and illustrates an example configuration.
Figure 2:
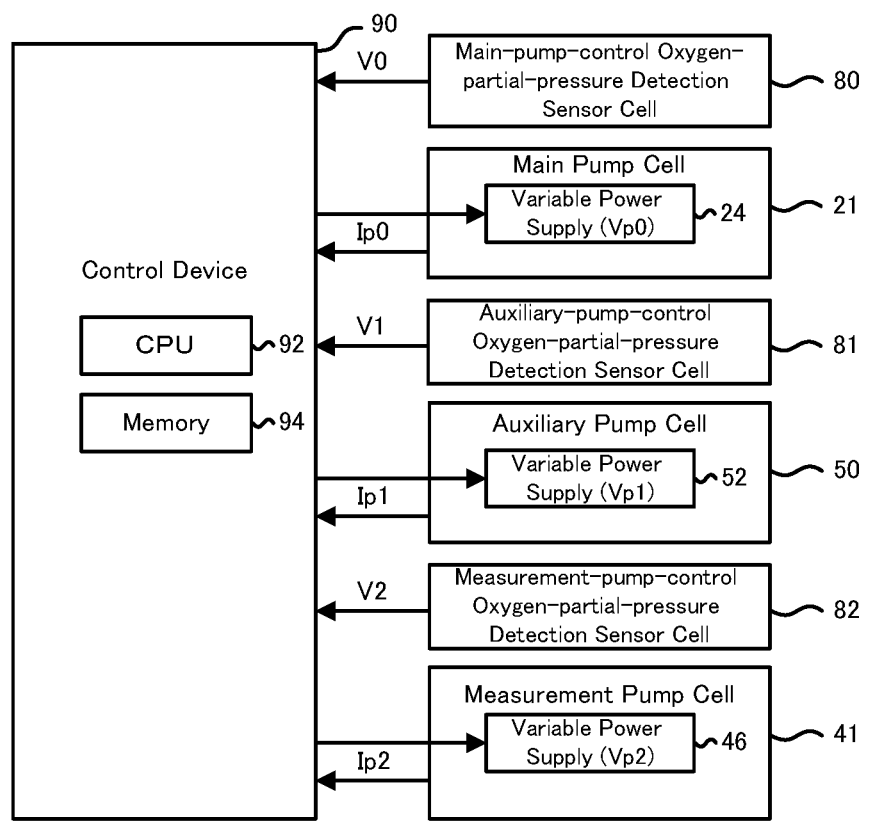
FIG. 2 is a block diagram of an example of a control device 90.

Preferred embodiments of the present invention will be described below with reference to the drawings. FIG. 1 is a schematic cross-sectional view of a gas sensor 100 and illustrates an example configuration. FIG. 2 is a block diagram of an example of a control device 90.

The gas sensor 100 is attached to, for example, a pipe, such as an exhaust gas pipe of an internal combustion engine, and used to measure the concentration of a specific gas, such as NOx, $NH_3$, etc., contained in the exhaust gas, which is a measurement-object gas. This embodiment assumes that the gas sensor 100 measures the NOx concentration as the concentration of the specific gas. The gas sensor 100 mainly includes a sensor element 101 and the control device 90 (see FIG. 2).

The sensor element 101 is an element having a layered body in which six layers, namely, a first substrate layer 1, a second substrate layer 2, a third substrate layer 3, a first solid electrolyte layer 4, a spacer layer 5, and a second solid electrolyte layer 6, each formed of a layer of an oxygen-ion-conductive solid electrolyte, such as zirconia ($ZrO_2$), are stacked in this order from the lower side as viewed in FIG. 1. The solid electrolyte used to form these six layers is dense and gastight. The sensor element 101 is manufactured by, for example, subjecting ceramic green sheets for the respective layers to predetermined processing, printing circuit patterns on the sheets, and thereafter, stacking and firing the sheets so as to be integrated.

On the front end side of the sensor element 101 (on the left end side in FIG. 1), between the lower surface of the second solid electrolyte layer 6 and the upper surface of the first solid electrolyte layer 4, a gas inlet 10, a first diffusion control portion 11, a buffer space 12, a second diffusion control portion 13, a first internal cavity 20, a third diffusion control portion 30, a second internal cavity 40, a fourth diffusion control portion 60, and a third internal cavity 61 are formed adjacent to each other in this order so as to communicate with each other.

The gas inlet 10, the buffer space 12, the first internal cavity 20, the second internal cavity 40, and the third internal cavity 61 are spaces, inside the sensor element 101, that are provided by hollowing the spacer layer 5 and have an upper portion that is defined by the lower surface of the second solid electrolyte layer 6, a lower portion that is defined by the upper surface of the first solid electrolyte layer 4, and sides that are defined by side surfaces of the spacer layer 5.

The first diffusion control portion 11, the second diffusion control portion 13, and the third diffusion control portion 30 are each provided as two horizontally long slits (the longitudinal direction of the openings is perpendicular to the drawing). The fourth diffusion control portion 60 is provided as one horizontally long slit (the longitudinal direction of the opening is perpendicular to the drawing) that is formed as a gap from the lower surface of the second solid electrolyte layer 6. Note that the portion from the gas inlet 10 up to the third internal cavity 61 is also called a measurement-object gas flowing portion.

At a location farther from the front end side than the measurement-object gas flowing portion, a reference gas inlet space 43 is provided in a portion between the upper surface of the third substrate layer 3 and the lower surface of the spacer layer 5, the portion having sides defined by side surfaces of the first solid electrolyte layer 4. As a reference gas that is used when the NOx concentration is measured, for example, the air is introduced into the reference gas inlet space 43.

An air inlet layer 48 is a layer formed of porous ceramic and allows the reference gas to be introduced into the air inlet layer 48 via the reference gas inlet space 43. The air inlet layer 48 is formed so as to cover a reference electrode 42.

The reference electrode 42 is an electrode formed so as to be sandwiched between the upper surface of the third substrate layer 3 and the first solid electrolyte layer 4, and the air inlet layer 48 that is connected to the reference gas inlet space 43 is provided around the reference electrode 42, as described above. As described below, the reference electrode 42 can be used to measure the oxygen concentration (oxygen partial pressure) in the first internal cavity 20, the second internal cavity 40, and the third internal cavity 61. The reference electrode 42 is formed of a porous cermet electrode (for example, a cermet electrode of Pt and $ZrO_2$).

In the measurement-object gas flowing portion, the gas inlet 10 is a portion open to the external space and allows the measurement-object gas to be taken into the sensor element 101 from the external space via the gas inlet 10. The first diffusion control portion 11 is a portion that applies a predetermined diffusion resistance to the measurement-object gas taken in via the gas inlet 10. The buffer space 12 is a space provided in order to guide the measurement-object gas introduced from the first diffusion control portion 11 toward the second diffusion control portion 13. The second diffusion control portion 13 is a portion that applies a predetermined diffusion resistance to the measurement-object gas that is introduced from the buffer space 12 toward the first internal cavity 20. In a case where the measurement-object gas is introduced into the first internal cavity 20 from outside the sensor element 101, the measurement-object gas that is abruptly taken into the sensor element 101 via the gas inlet 10 by pressure fluctuations of the measurement-object gas in the external space (in a case where the measurement-object gas is an exhaust gas of an automobile, pulsations of the exhaust gas pressure) is not directly introduced into the first internal cavity 20 but is introduced into the first internal cavity 20 after concentration fluctuations of the measurement-object gas have been cancelled in the first diffusion control portion 11, the buffer space 12, and the second diffusion control portion 13. Accordingly, the concentration fluctuations of the measurement-object gas that is introduced into the first internal cavity 20 are decreased to a level that requires almost no attention. The first internal cavity 20 is provided as a space for regulating the oxygen partial pressure of the measurement-object gas that is introduced via the second diffusion control portion 13. The oxygen partial pressure is regulated by an operation of a main pump cell 21.

The main pump cell 21 is an electrochemical pump cell constituted by an inside pump electrode 22, an outside pump electrode 23, and the second solid electrolyte layer 6 sandwiched between these electrodes. The inside pump electrode 22 has a ceiling electrode portion 22a that is provided on the lower surface of the second solid electrolyte layer 6 in almost the entire portion that faces the first internal cavity 20. The outside pump electrode 23 is provided on the upper surface of the second solid electrolyte layer 6 in an area corresponding to the ceiling electrode portion 22a so as to expose to the external space.

The inside pump electrode 22 is formed so as to extend across the upper and lower solid electrolyte layers (the second solid electrolyte layer 6 and the first solid electrolyte layer 4), which define the first internal cavity 20, and the spacer layer 5, which provides side walls. Specifically, the ceiling electrode portion 22a is formed on the lower surface of the second solid electrolyte layer 6, the lower surface providing the ceiling surface of the first internal cavity 20, and a bottom electrode portion 22b is formed on the upper surface of the first solid electrolyte layer 4, the upper surface providing the bottom surface of the first internal cavity 20. Further, side electrode portions (not illustrated) are formed on side wall surfaces (internal surfaces) of the spacer layer 5 that constitute the respective side wall portions of the first internal cavity 20 so as to connect the ceiling electrode portion 22a and the bottom electrode portion 22b with each other. The inside pump electrode 22 is thus disposed so as to have a tunnel structure in the portion where the side electrode portions are disposed.

The inside pump electrode 22 and the outside pump electrode 23 are each formed of a porous cermet electrode (for example, a cermet electrode of Pt and $ZrO_2$ containing 1% Au). Note that the inside pump electrode 22 that is in contact with the measurement-object gas is formed by using a material having a lowered reduction ability for NOx components in the measurement-object gas.

In the main pump cell 21, a desired pump voltage Vp0 is applied between the inside pump electrode 22 and the outside pump electrode 23 to provide a pump current Ip0 between the inside pump electrode 22 and the outside pump electrode 23 in the positive direction or the negative direction, so that oxygen inside the first internal cavity 20 can be pumped out to the external space or oxygen in the external space can be pumped into the first internal cavity 20.

Further, in order to detect the oxygen concentration (oxygen partial pressure) of the atmosphere in the first internal cavity 20, the inside pump electrode 22, the second solid electrolyte layer 6, the spacer layer 5, the first solid electrolyte layer 4, the third substrate layer 3, and the reference electrode 42 constitute an electrochemical sensor cell, that is, a main-pump-control oxygen-partial-pressure detection sensor cell 80.

When an electromotive force V0 in the main-pump-control oxygen-partial-pressure detection sensor cell 80 is measured, the oxygen concentration (oxygen partial pressure) in the first internal cavity 20 can be determined. Further, the pump voltage Vp0 of a variable power supply 24 is controlled by feedback control so that the electromotive force V0 matches a target value to thereby control the pump current Ip0. Accordingly, the oxygen concentration in the first internal cavity 20 can be kept at a predetermined constant value.

The third diffusion control portion 30 is a portion that applies a predetermined diffusion resistance to the measurement-object gas for which the oxygen concentration (oxygen partial pressure) is controlled in the first internal cavity 20 by an operation of the main pump cell 21 and guides the measurement-object gas to the second internal cavity 40.

The oxygen concentration (oxygen partial pressure) of the measurement-object gas is regulated in advance in the first internal cavity 20, and thereafter, the measurement-object gas is introduced into the second internal cavity 40 via the third diffusion control portion 30. The second internal cavity 40 is provided as a space for allowing an auxiliary pump cell 50 to further regulate the oxygen partial pressure of the measurement-object gas. Accordingly, the oxygen concentration in the second internal cavity 40 can be kept constant with a high accuracy, which enables highly accurate measurement of the NOx concentration in the gas sensor 100.

The auxiliary pump cell 50 is an auxiliary electrochemical pump cell constituted by an auxiliary pump electrode 51, the outside pump electrode 23, and the second solid electrolyte layer 6. The auxiliary pump electrode 51 has a ceiling electrode portion 51a that is provided on the lower surface of the second solid electrolyte layer 6 in almost the entire portion that faces the second internal cavity 40. The outside pump electrode 23 need not be used, and any appropriate electrode on the outside of the sensor element 101 may be used.

The auxiliary pump electrode 51 has a tunnel structure similar to that of the inside pump electrode 22 provided in the first internal cavity 20 described above, and is disposed in the second internal cavity 40. That is, the ceiling electrode portion 51a is formed on the second solid electrolyte layer 6, which provides the ceiling surface of the second internal cavity 40, and a bottom electrode portion 51b is formed on the first solid electrolyte layer 4, which provides the bottom surface of the second internal cavity 40. Further, side electrode portions (not illustrated) that couples the ceiling electrode portion 51a and the bottom electrode portion 51b with each other are formed on side wall surfaces of the spacer layer 5 that provide the respective side walls of the second internal cavity 40 to thereby form the tunnel structure. Note that, similarly to the inside pump electrode 22, also the auxiliary pump electrode 51 is formed by using a material having a lowered reduction ability for NOx components in the measurement-object gas.

In the auxiliary pump cell 50, a desired voltage Vp1 is applied between the auxiliary pump electrode 51 and the outside pump electrode 23, so that oxygen in the atmosphere inside the second internal cavity 40 can be pumped out to the external space or oxygen in the external space can be pumped into the second internal cavity 40.

Further, in order to control the oxygen partial pressure of the atmosphere inside the second internal cavity 40, the auxiliary pump electrode 51, the reference electrode 42, the second solid electrolyte layer 6, the spacer layer 5, the first solid electrolyte layer 4, and the third substrate layer 3 constitute an electrochemical sensor cell, that is, an auxiliary-pump-control oxygen-partial-pressure detection sensor cell 81.

Note that the auxiliary-pump-control oxygen-partial-pressure detection sensor cell 81 detects an electromotive force V1, and the voltage of a variable power supply 52 is controlled on the basis of the electromotive force V1 to allow the auxiliary pump cell 50 to perform pumping. Accordingly, the oxygen partial pressure of the atmosphere inside the second internal cavity 40 is controlled to a low partial pressure that has substantially no effect on NOx measurement.

In addition to this, the pump current Ip1 is used to control the electromotive force of the main-pump-control oxygen-partial-pressure detection sensor cell 80.

Specifically, the pump current Ip1 is input to the main-pump-control oxygen-partial-pressure detection sensor cell 80 as a control signal, and the electromotive force V0 is controlled to thereby control the slope of the oxygen partial pressure of the measurement-object gas that is introduced into the second internal cavity 40 from the third diffusion control portion 30 so as to be always kept constant. In a case of use as a NOx sensor, the main pump cell 21 and the auxiliary pump cell 50 work to keep the oxygen concentration in the second internal cavity 40 at a constant value of about 0.001 ppm.

The fourth diffusion control portion 60 is a portion that applies a predetermined diffusion resistance to the measurement-object gas for which the oxygen concentration (oxygen partial pressure) is controlled in the second internal cavity 40 by an operation of the auxiliary pump cell 50 and guides the measurement-object gas to the third internal cavity 61. The fourth diffusion control portion 60 is responsible for limiting the amount of NOx that flows into the third internal cavity 61.

The oxygen concentration (oxygen partial pressure) of the measurement-object gas is regulated in advance in the second internal cavity 40, and thereafter, the measurement-object gas is introduced into the third internal cavity 61 via the fourth diffusion control portion 60. The third internal cavity 61 is provided as a space for performing processing relating to measurement of the concentration of nitrogen oxides (NOx) in the measurement-object gas. The NOx concentration is measured mainly in the third internal cavity 61 by an operation of a measurement pump cell 41.

The measurement pump cell 41 measures the NOx concentration of the measurement-object gas in the third internal cavity 61. The measurement pump cell 41 is an electrochemical pump cell constituted by a measurement electrode 44 that is provided on the upper surface of the first solid electrolyte layer 4 in a portion that faces the third internal cavity 61, the outside pump electrode 23, the second solid electrolyte layer 6, the spacer layer 5, and the first solid electrolyte layer 4. The measurement electrode 44 is a porous cermet electrode formed of a material for which a reduction ability for NOx components in the measurement-object gas is made higher than that of the inside pump electrode 22. The measurement electrode 44 also functions as a NOx reduction catalyst for reducing NOx present in the atmosphere inside the third internal cavity 61.

In the measurement pump cell 41, oxygen generated as a result of decomposition of nitrogen oxides in the atmosphere around the measurement electrode 44 can be pumped out, and the amount of generated oxygen can be detected as a pump current Ip2.

In order to detect the oxygen partial pressure around the measurement electrode 44, the first solid electrolyte layer 4, the third substrate layer 3, the measurement electrode 44, and the reference electrode 42 constitute an electrochemical sensor cell, that is, a measurement-pump-control oxygen-partial-pressure detection sensor cell 82. The measurement-pump-control oxygen-partial-pressure detection sensor cell 82 detects an electromotive force V2, and a variable power supply 46 is controlled on the basis of the electromotive force V2.

The measurement-object gas that is guided into the second internal cavity 40 reaches the measurement electrode 44 in the third internal cavity 61 via the fourth diffusion control portion 60 in a state where the oxygen partial pressure is controlled. Nitrogen oxides in the measurement-object gas around the measurement electrode 44 are reduced ($2NO \rightarrow N_2+O_2$) to generate oxygen. The generated oxygen is pumped by the measurement pump cell 41. At this time, the voltage Vp2 of the variable power supply 46 is controlled so that the electromotive force V2 detected by the measurement-pump-control oxygen-partial-pressure detection sensor cell 82 is kept constant. The amount of oxygen generated around the measurement electrode 44 is proportional to the concentration of nitrogen oxides in the measurement-object gas, and therefore, the concentration of nitrogen oxides in the measurement-object gas is calculated by using the pump current Ip2 in the measurement pump cell 41.

When the measurement electrode 44, the first solid electrolyte layer 4, the third substrate layer 3, and the reference electrode 42 are combined to form an oxygen-partial-pressure detector that functions as an electrochemical sensor cell, an electromotive force corresponding to the difference between the amount of oxygen generated as a result of reduction of NOx components in the atmosphere around the measurement electrode 44 and the amount of oxygen contained in the reference air can be detected, from which the concentration of NOx components in the measurement-object gas can be calculated.

Further, the second solid electrolyte layer 6, the spacer layer 5, the first solid electrolyte layer 4, the third substrate layer 3, the outside pump electrode 23, and the reference electrode 42 constitute an electrochemical sensor cell 83, and an electromotive force Vref obtained by the sensor cell 83 can be used to detect the oxygen partial pressure of the measurement-object gas outside the sensor.

In the gas sensor 100 configured as described above, the main pump cell 21 and the auxiliary pump cell 50 are operated to provide, to the measurement pump cell 41, the measurement-object gas for which the oxygen partial pressure is always kept at a constant low value (a value having substantially no effect on NOx measurement). Therefore, on the basis of the pump current Ip2 that flows substantially in proportion to the concentration of NOx in the measurement-object gas when oxygen generated as a result of reduction of NOx is pumped out by the measurement pump cell 41, the NOx concentration of the measurement-object gas can be determined.

Further, the sensor element 101 includes a heater portion 70 that is responsible for temperature control, that is, heats the sensor element 101 and conserves heat, in order to increase the oxygen ion conductivity of the solid electrolyte. The heater portion 70 includes a heater connector electrode 71, a heater 72, a through hole 73, a heater insulation layer 74, and a pressure relieving hole 75.

The heater connector electrode 71 is an electrode formed so as to be in contact with the lower surface of the first substrate layer 1. When the heater connector electrode 71 is connected to an external power supply, the heater portion 70 is externally supplied with power.

The heater 72 is an electrical resistor that is formed so as to be sandwiched between the second substrate layer 2 below and the third substrate layer 3 above. The heater 72 is connected to the heater connector electrode 71 via the through hole 73, generates heat when power is externally supplied via the heater connector electrode 71, and heats the solid electrolyte that forms the sensor element 101 and conserves heat.

The heater 72 is buried so as to extend across the entire area from the first internal cavity 20 to the third internal cavity 61 and can control the temperature of the entire sensor element 101 so that the above-described solid electrolyte is activated.

The heater insulation layer 74 is an insulation layer formed on the upper and lower surfaces of the heater 72 by using an insulating material, such as alumina. The heater insulation layer 74 is formed in order to achieve electrical insulation between the second substrate layer 2 and the heater 72 and electrical insulation between the third substrate layer 3 and the heater 72.

The pressure relieving hole 75 is a portion that is provided so as to penetrate the third substrate layer 3 and the air inlet layer 48 and so as to communicate with the reference gas inlet space 43, and is formed in order to relieve an increased internal pressure associated with an increase in the temperature inside the heater insulation layer 74.

The control device 90 is a general microprocessor that includes a CPU 92, a memory 94, etc. The control device 90 receives the electromotive force V0 detected by the main-pump-control oxygen-partial-pressure detection sensor cell 80, the electromotive force V1 detected by the auxiliary-pump-control oxygen-partial-pressure detection sensor cell 81, the electromotive force V2 detected by the measurement-pump-control oxygen-partial-pressure detection sensor cell 82, the current Ip0 detected by the main pump cell 21, the current Ip1 detected by the auxiliary pump cell 50, and the current Ip2 detected by the measurement pump cell 41. The control device 90 outputs control signals to the variable power supply 24 of the main pump cell 21, the variable power supply 52 of the auxiliary pump cell 50, and the variable power supply 46 of the measurement pump cell 41.

The control device 90 controls the pump voltage Vp0 of the variable power supply 24 by feedback control so that the electromotive force V0 matches a target value. Accordingly, the pump current Ip0 changes in accordance with the oxygen concentration of the measurement-object gas, and thus, the air-fuel ratio (A/F) of the measurement-object gas. As a consequence, the control device 90 can calculate the oxygen concentration and A/F of the measurement-object gas on the basis of the pump current Ip0.

The control device 90 controls the voltage Vp1 of the variable power supply 52 by feedback control so as to keep the electromotive force V1 constant (that is, to keep the oxygen concentration in the second internal cavity 40 at a predetermined low oxygen concentration that has substantially no effect on NOx measurement). In addition, the control device 90 sets a target value of the electromotive force V0 on the basis of the pump current Ip1. Accordingly, the slope of the oxygen partial pressure of the measurement-object gas that is introduced into the second internal cavity 40 from the third diffusion control portion 30 is always kept constant.

Further, the control device 90 controls the voltage Vp2 of the variable power supply 46 by feedback control so that the electromotive force V2 is kept constant (so that the concentration of oxygen generated as a result of reduction of nitrogen oxides in the measurement-object gas in the third internal cavity 61 becomes substantially zero), and calculates the concentration of nitrogen oxides in the measurement-object gas on the basis of the pump current Ip2.

The present inventors have measured the concentration of nitrogen oxides contained in the measurement-object gas in a rich atmosphere (an atmosphere in which oxygen is not contained but an unburned fuel is contained) by using the gas sensor 100 and studied the behavior of the pump current Ip2 at that time. As the measurement-object gas in a rich atmosphere, a model gas has been adjusted and used. For the model gas, nitrogen has been used as a base gas, an ethylene gas has been used as a fuel gas, the temperature has been set to 260°, the flow rate has been set to 50 L/min, and the amount of moisture addition has been set to 3 volume %, and the model gas has been adjusted so that the oxygen concentration is within a range from −11 to 0 volume % (A/F is within a range from 11 to 14) and the NO concentration is within a range from 0 to 500 volume ppm. The diameter of a pipe used to provide the model gas has been set to 20 mm. Note that a conversion formula for the oxygen concentration and A/F is well known (see, for example, Brettschneider, Johannes, "Berechnung des Liftverhaeltnisses λ von Luft-Kraftstoff-Gemsichen and des Einflusses von Meβfehlern auf λ", Bosch Technische Berichte, Band 6, Heft 4, Seite 177-186, Stuttgart, 1979).

Figure 3:
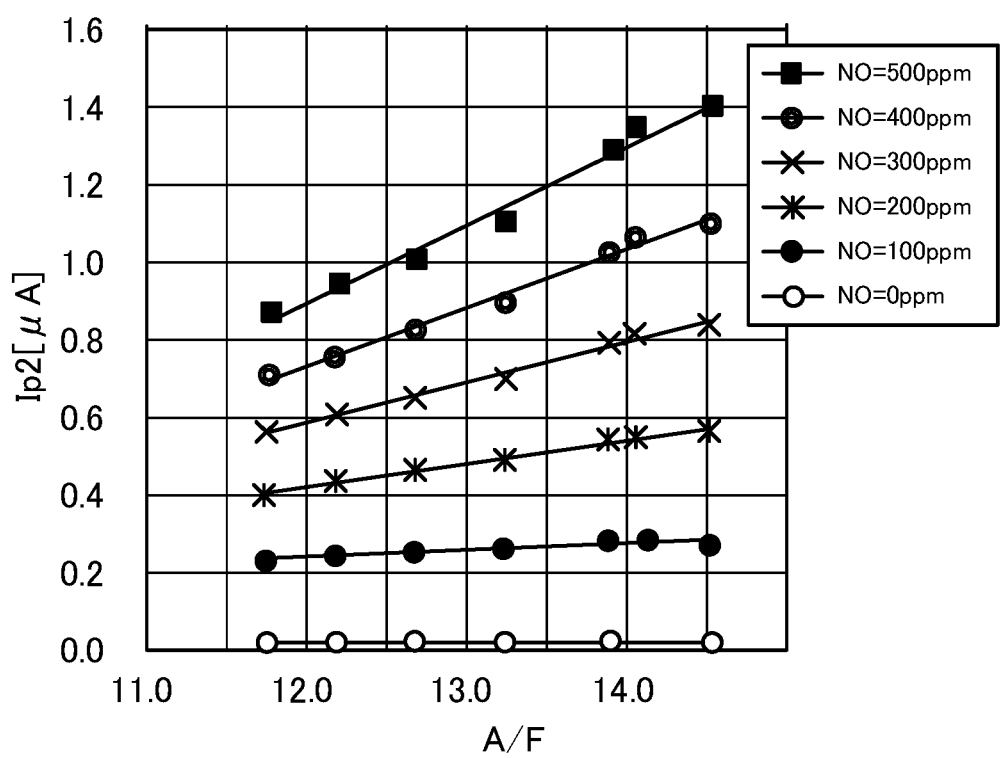
FIG. 3 is a graph indicating a relationship between A/F and a pump current Ip2 when the NO concentration is kept constant.

FIG. 3 is a graph indicating a relationship between A/F and the pump current Ip2 when the NO concentration is kept constant. As found from FIG. 3, when the actual concentration of the NO gas is kept constant, the pump current Ip2 linearly changes relative to A/F of the measurement-object gas. That is, the pump current Ip2 is approximated by a linear function of A/F. The slope and the intercept of this linear function differ depending on the actual concentration of the NO gas.

Figure 4:
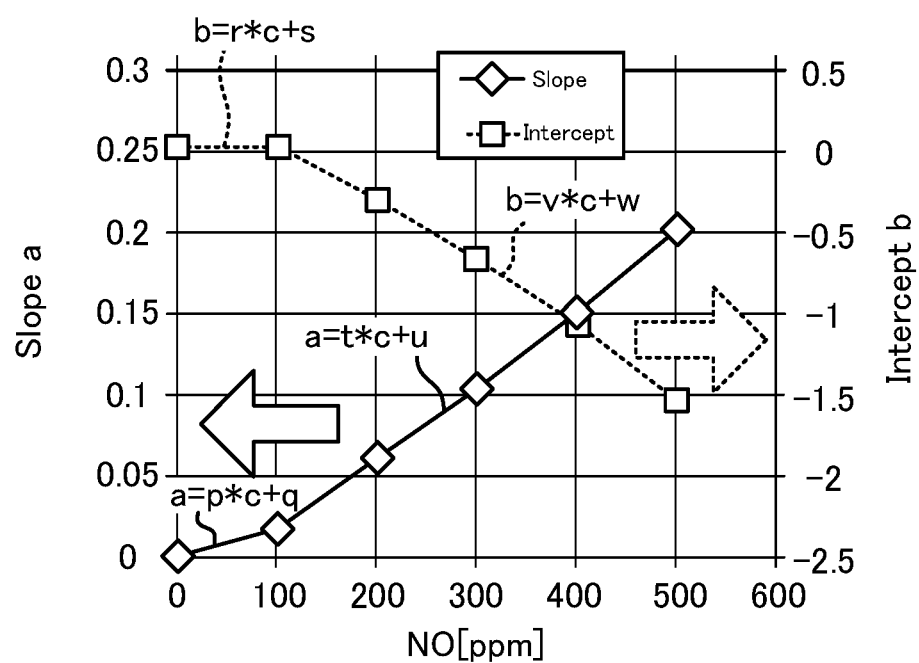
FIG. 4 is a graph obtained by plotting the slope a and the intercept b of a linear function expression for each value of the NO concentration.

FIG. 4 is a graph obtained by plotting the slope a and the intercept b of the linear function expression for each value of the NO concentration. As found from FIG. 4, when the NO concentration is within a range from 0 to 100 volume ppm (within a predetermined low concentration range), the slope a is expressed by a=p*c+q (where c is the NO concentration, and p and q are constants), and the intercept b is expressed by b=r*c+s (where c is the NO concentration, and r and s are constants). When the NO concentration is within a range from 100 to 500 volume ppm (exceeds the predetermined low concentration range), the slope a is expressed by a=t*c+u (where c is the NO concentration, and t and u are constants), and the intercept b is expressed by b=c+w (where c is the NO concentration, and v and w are constants).

Therefore, the pump current Ip2 is expressed by expression (1) below when the NO concentration is within a range from 0 to 100 volume ppm, and is expressed by expression (2) below when the NO concentration is within a range from 100 to 500 volume ppm. Such relationships between the NO concentration and the calculation expressions for the pump current Ip2 are stored in the memory 94 of the control device 90.

$$Ip2=(p*c+q)*R+(r*c+s) \text{(where } R \text{ is } A/F, \text{ and } p,q,r, \text{ and } s \text{ are constants)} \quad (1)$$

$$Ip2=(t*c+u)*R+(v*c+w) \text{(where } R \text{ is } A/F, \text{ and } t,u,v, \text{ and } w \text{ are constants)} \quad (2)$$

Figure 5:
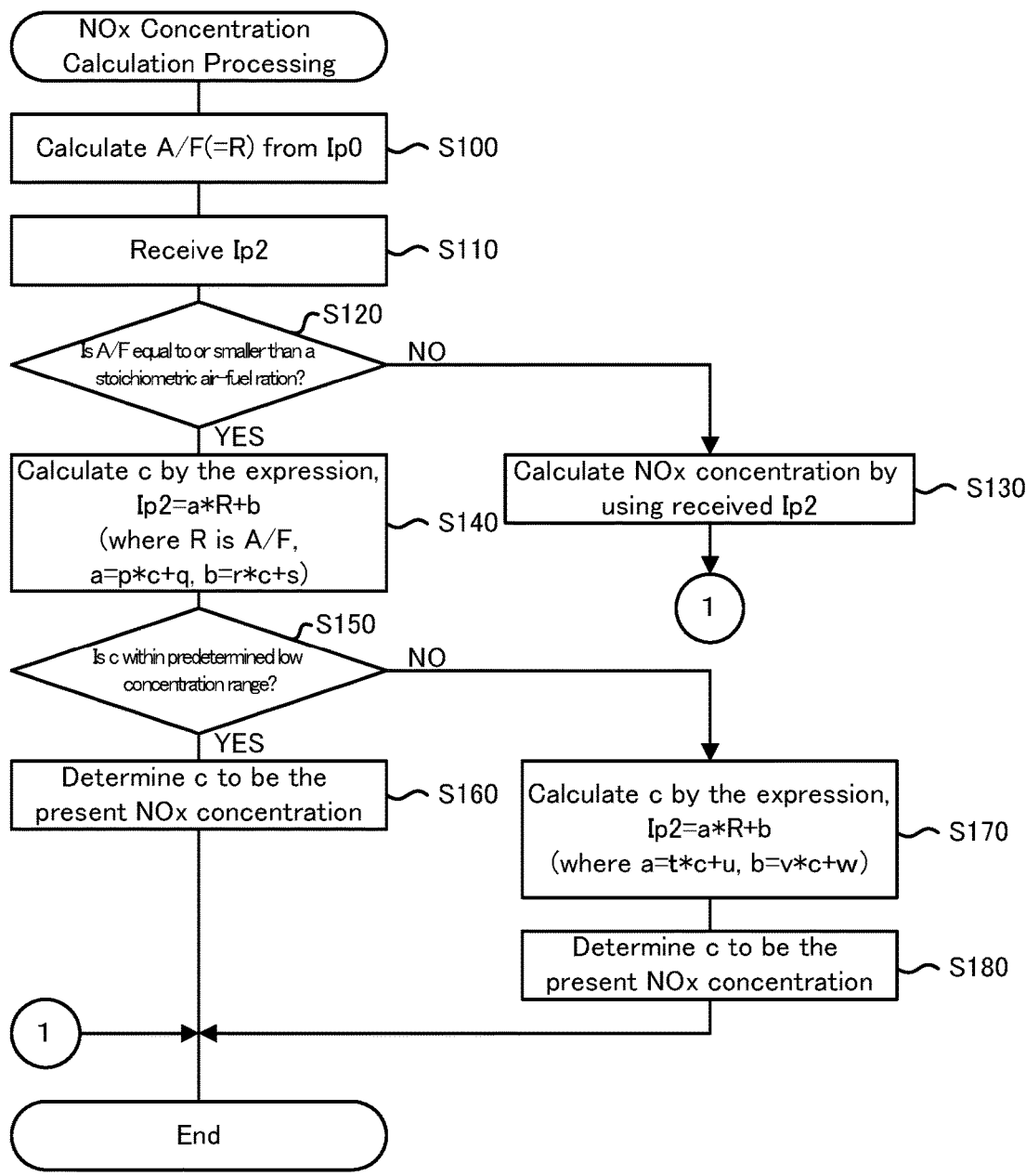
FIG. 5 is a flowchart illustrating example NOx concentration calculation processing.

Now, example calculation of the concentration of nitrogen oxides by the CPU 92 of the control device 90 is described with reference to FIG. 5. FIG. 5 is a flowchart illustrating example NOx concentration calculation processing.

When this processing is started, the CPU 92 first calculates A/F (hereinafter A/F may be represented by R) from the pump current Ip0 of the main pump cell 21 (S100). Next, the CPU 92 receives the pump current Ip2 of the measurement pump cell 41 (S110). Next, the CPU 92 determines whether A/F is equal to or smaller than a stoichiometric air-fuel ratio, that is, whether the measurement-object gas is in a rich atmosphere (S120). If A/F exceeds the stoichiometric air-fuel ratio, that is, if the measurement-object gas is in a lean atmosphere, the CPU 92 uses the pump current Ip2 as is without correction to calculate the NOx concentration of the measurement-object gas (S130), and this routine ends.

On the other hand, if A/F is determined to be equal to or smaller than the stoichiometric air-fuel ratio in S120, the CPU 92 uses expression (1) to calculate the NOx concentration, that is, c [volume ppm] (S140). In expression (1), the pump current Ip2 is a measurement value, R is a calculation value, and p, q, r, and s are constants while only c is a variable, and therefore, c can be calculated. Next, the CPU 92 determines whether the calculated value of c is within a predetermined low concentration range (here, from 0 to 100 [volume ppm]) (S150). If the value of c is within the predetermined low concentration range, the CPU 92 determines the value of c to be the present NOx concentration (S160), and the routine ends.

On the other hand, if the value of c is determined to exceed the predetermined low concentration range in S150, the CPU 92 uses expression (2) to calculate the NOx concentration, that is, c [volume ppm] (S170). In expression (2), the pump current Ip2 is a measurement value, R is a calculation value, and t, u, v, and w are constants while only c is a variable, and therefore, c can be calculated. Thereafter, the CPU 92 determines the value of C calculated in S170 to be the present NOx concentration (S180), and the routine ends.

Here, correspondences between the constituent elements of this embodiment and the constituent elements of the present invention are clarified. The layered body of this embodiment in which the six layers, namely, the first substrate layer 1, the second substrate layer 2, the third substrate layer 3, the first solid electrolyte layer 4, the spacer layer 5, and the second solid electrolyte layer 6, are stacked in this order corresponds to a layered body of the present invention. The measurement electrode 44 of this embodiment corresponds to a measurement electrode of the present invention. The CPU 92 of the control device 90 of this embodiment corresponds to a specific-gas concentration detector and a corrector of the present invention. The third internal cavity 61 of this embodiment corresponds to a measurement chamber of the present invention. The first internal cavity 20 of this embodiment corresponds to an oxygen concentration regulating chamber of the present invention. The pump current Ip0 of this embodiment corresponds to a regulating pump current of the present invention. The CPU 92 of the control device 90 of this embodiment corresponds to an oxygen concentration detector of the present invention. The memory 94 of the control device 90 of this embodiment corresponds to a storage unit of the present invention.

According to this embodiment described above, when the measurement-object gas is in a rich atmosphere, c [volume ppm], which is the NOx concentration, is corrected on the basis of A/F of the measurement-object gas. Here, when the measurement-object gas is in a rich atmosphere, even if the actual concentration of NOx contained in the measurement-object gas remains the same, the pump current Ip2 changes in accordance with A/F of the measurement-object gas, and therefore, the detected NOx concentration also changes. Therefore, the accuracy of NOx measurement decreases. This has been newly found by the present inventors this time. Accordingly, when the measurement-object gas is in a rich atmosphere, the NOx concentration is corrected on the basis of A/F of the measurement-object gas. As a consequence, the accuracy of measurement of NOx contained in the measurement-object gas in a rich atmosphere increases.

Further, the gas sensor 100 can detect A/F of the measurement-object gas. Therefore, the number of sensors can be made smaller than that in a case where the gas sensor 100 receives A/F detected by a sensor other than the gas sensor 100.

Further, correspondences between the concentration of NOx contained in the measurement-object gas, A/F of the measurement-object gas, and the pump current Ip2 of the measurement pump cell 41 when the measurement-object gas is in a rich atmosphere are stored in advance in the memory 94 of the control device 90, and the CPU 92 uses the correspondences to make a correction. Accordingly, the correction can be made with a higher accuracy.

Second Embodiment

In this embodiment, a case of measuring the concentration of ammonia contained in the measurement-object gas is described. Here, the gas sensor 100 similar to that in the first embodiment is used. Ammonia contained in the measurement-object gas is oxidized and converted to NO in the first internal cavity 20. Then, NO obtained as a result of conversion passes through the second internal cavity 40 and is introduced into the third internal cavity 61, which is a measurement chamber. Therefore, ammonia concentration measurement is performed basically on the basis of a theory the same as that for NOx concentration measurement.

Figure 6:
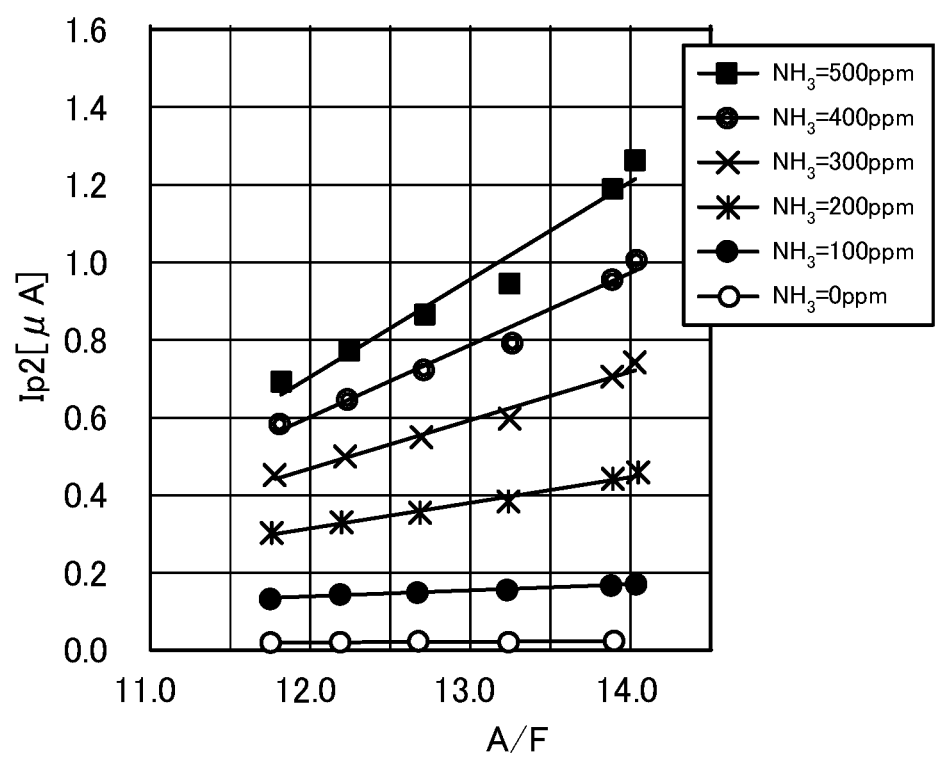
FIG. 6 is a graph indicating a relationship between A/F and the pump current Ip2 when the ammonia concentration is kept constant.

FIG. 6 is a graph indicating a relationship between A/F and the pump current Ip2 when the ammonia concentration is kept constant. As found from FIG. 6, when the actual concentration of the ammonia gas is kept constant, the pump current Ip2 linearly changes relative to A/F of the measurement-object gas. That is, the pump current Ip2 is approximated by a linear function of A/F. The slope and the intercept of this linear function differ depending on the actual concentration of the ammonia gas.

Figure 7:
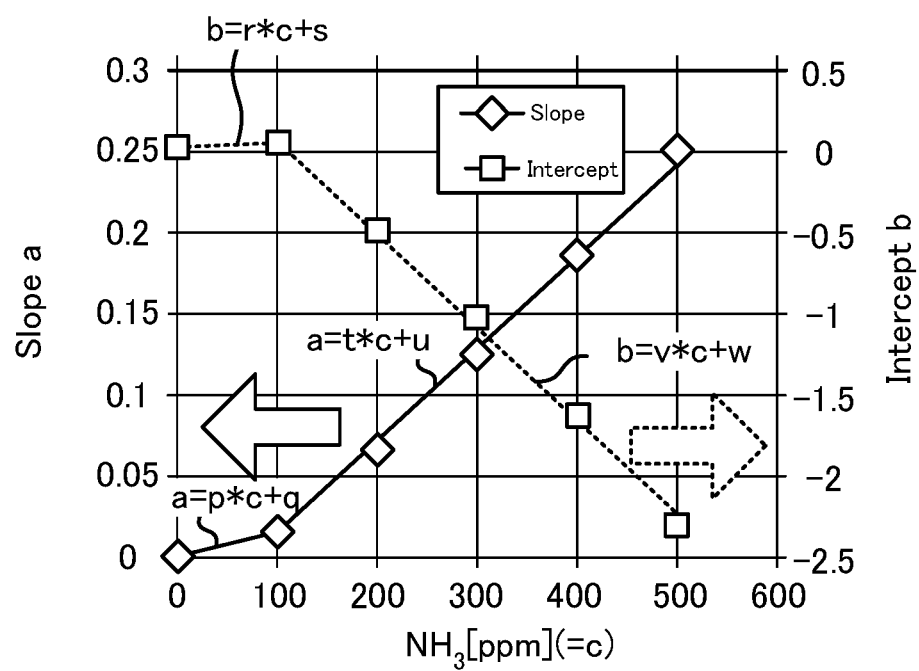
FIG. 7 is a graph obtained by plotting the slope a and the intercept b of a linear function expression for each value of the ammonia concentration.

FIG. 7 is a graph obtained by plotting the slope a and the intercept b of the linear function expression for each value of the ammonia concentration. As found from FIG. 7, when the ammonia concentration is within a range from 0 to 100 volume ppm (within a predetermined low concentration range), the slope a is expressed by a=p*c+q (where c is the ammonia concentration, and p and q are constants), and the intercept b is expressed by b=r*c+s (where c is the ammonia concentration, and r and s are constants). When the ammonia concentration is within a range from 100 to 500 volume ppm (exceeds the predetermined low concentration range), the slope a is expressed by a=t*c+u (where c is the ammonia concentration, and t and u are constants), and the intercept b is expressed by b=v*c+w (where c is the ammonia concentration, and v and w are constants). Note that the values of p, q, r, s, t, u, v, and w are different from the values in the first embodiment.

Therefore, the pump current Ip2 is expressed by expression (3) below when the ammonia concentration is within a range from 0 to 100 volume ppm, and is expressed by expression (4) below when the ammonia concentration is within a range from 100 to 500 volume ppm. Such relationships between the ammonia concentration and the calculation expressions for the pump current Ip2 are stored in the memory 94 of the control device 90.

$$Ip2=(p*c+q)*R+(r*c+s)\text{(where } R \text{ is } A/F, \text{ and } p,q,r, \text{ and } s \text{ are constants)} \quad (3)$$

$$Ip2=(t*c+u)*R+(v*c+w)\text{(where } R \text{ is } A/F, \text{ and } t,u,v, \text{ and } w \text{ are constants)} \quad (4)$$

The procedure for the CPU 92 of the control device 90 to calculate the ammonia concentration is similar to that illustrated as the flowchart in FIG. 5 of the first embodiment except that expressions (3) and (4) are used instead of expressions (1) and (2) and that the ammonia concentration is calculated instead of the NOx concentration, and therefore, a description thereof will be omitted here.

According to this embodiment described above, when the measurement-object gas is in a rich atmosphere, c [volume ppm], which is the ammonia concentration, is corrected on the basis of A/F of the measurement-object gas. Here, when the measurement-object gas is in a rich atmosphere, even if the actual concentration of ammonia contained in the measurement-object gas remains the same, the pump current Ip2 changes in accordance with A/F of the measurement-object gas, and therefore, the detected ammonia concentration also changes. Therefore, the accuracy of ammonia measurement decreases. This has been newly found by the present inventors this time. Accordingly, when the measurement-object gas is in a rich atmosphere, the ammonia concentration is corrected on the basis of A/F of the measurement-object gas. As a consequence, the accuracy of measurement of ammonia contained in the measurement-object gas in a rich atmosphere increases.

Further, the gas sensor 100 can detect A/F of the measurement-object gas. Therefore, the number of sensors can be made smaller than that in a case where the gas sensor 100 receives A/F detected by a sensor other than the gas sensor 100.

Further, correspondences between the concentration of ammonia contained in the measurement-object gas, A/F of the measurement-object gas, and the pump current Ip2 of the measurement pump cell 41 when the measurement-object gas is in a rich atmosphere are stored in advance in the memory 94 of the control device 90, and the CPU 92 uses the correspondences to make a correction. Accordingly, the correction can be made with a higher accuracy.

Third Embodiment

In this embodiment, similarly to the first embodiment, the case of measuring the concentration of NOx contained in the measurement-object gas is described. Here, the gas sensor 100 similar to that in the first embodiment is used.

Figure 8:
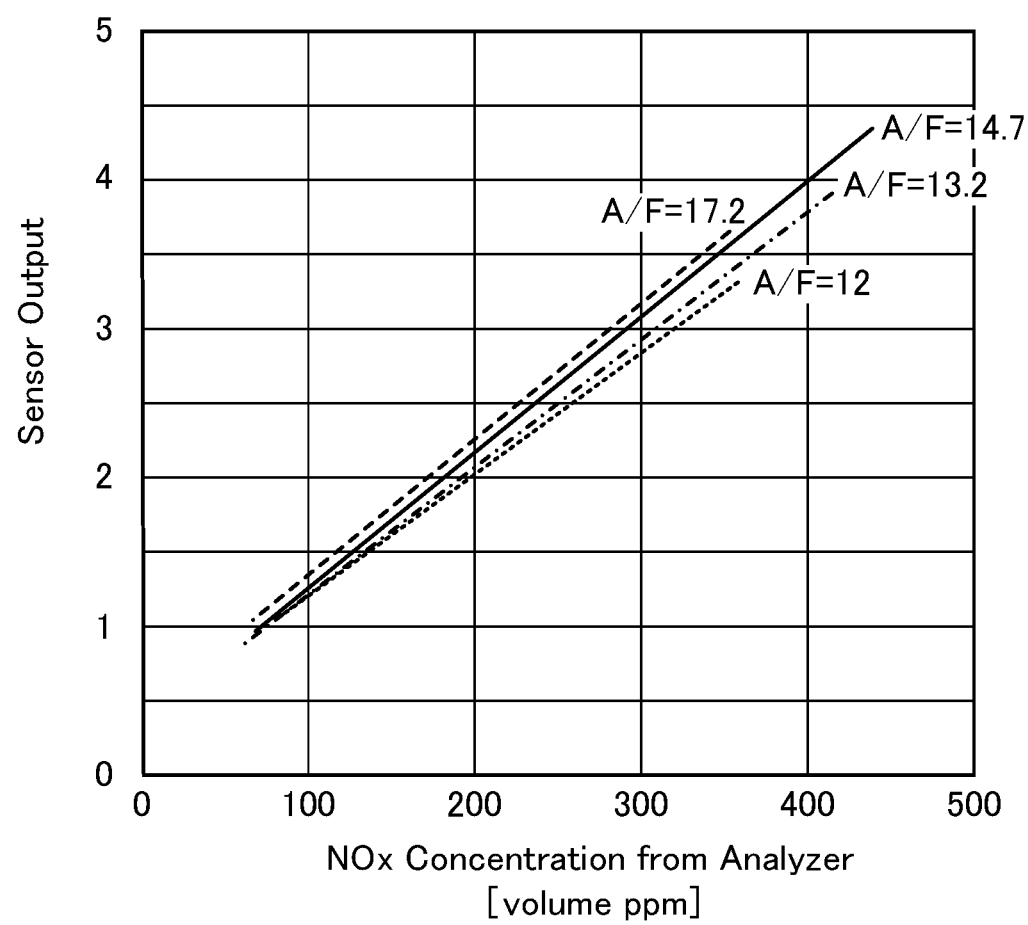
FIG. 8 is a graph indicating a relationship between the NOx concentration from an analyzer and a sensor output from the gas sensor 100.
Figure 9:
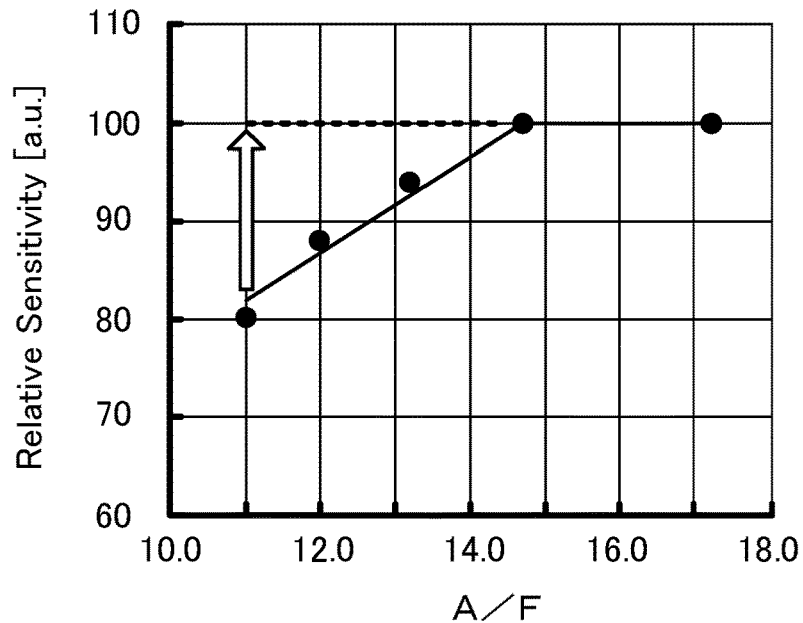
FIG. 9 is a graph indicating a correspondence between A/F of a measurement-object gas and a relative sensitivity.

The gas sensor 100 and a NOx analyzer have been connected to an exhaust pipe of an actual gasoline engine, the gas sensor 100 has been used to measure A/F of the measurement-object gas and to detect a sensor output (a voltage value [V] that indicates the NOx concentration linearly changing in accordance with the pump current Ip2 detected by the gas sensor 100), and the NOx analyzer has been used to detect the NOx concentration of the measurement-object gas. FIG. 8 is a graph indicating a relationship between the NOx concentration from the analyzer and the sensor output from the gas sensor 100 in the cases where A/F is equal to 17.2, 14.7, 13.2, and 12 respectively. It is found from FIG. 8 that the NOx concentration from the analyzer and the sensor output from the gas sensor 100 have a linear relationship for each value of A/F and that the sensor output can be approximated by a linear function of the NOx concentration from the analyzer. Further, as A/F decreases from a value close to a stoichiometric air-fuel ratio (A/F=14.7) to 13.2 and to 12, the sensitivity of the sensor output relative to the NOx concentration decreases. That is, the slope of an expression that expresses a linear function of the NOx concentration from the analyzer by which the sensor output is approximated becomes smaller as A/F decreases. Here, the percentage (%) of the actual sensor output relative to the sensor output when A/F is equal to the stoichiometric air-fuel ratio is called a relative sensitivity. FIG. 9 is a graph indicating a correspondence between A/F of the measurement-object gas and the relative sensitivity. As found from FIG. 9, in a rich atmosphere (an area in which A/F is smaller than 14.5), the relative sensitivity can be approximated by a linear function of A/F of the measurement-object gas. In the rich atmosphere, the sensitivity of the sensor output decreases, and therefore, the sensor output needs to be corrected so that the relative sensitivity is equal to 100. Specifically, a correction coefficient with which the relative sensitivity is equal to 100 is calculated for each value of A/F of the measurement-object gas and stored in advance in the memory 94 of the control device 90. The CPU 92 calculates a value of A/F on the basis of the pump current Ip0, reads a correction coefficient corresponding to the calculated value of A/F from the memory 94, multiples the sensor output from the gas sensor 100 by the correction coefficient, and uses the resulting value as the sensor output after correction.

Figure 10:
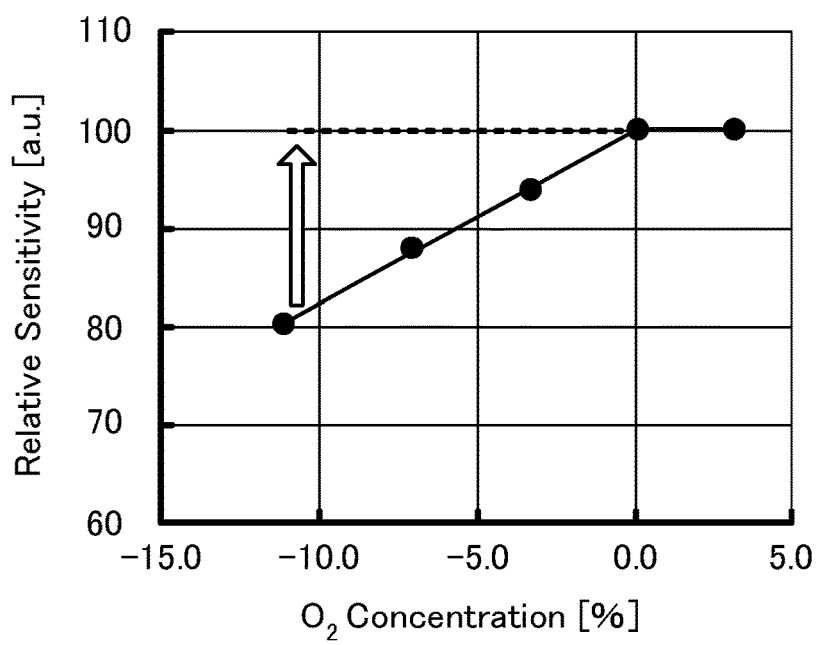
FIG. 10 is a graph indicating a correspondence between the oxygen concentration of a measurement-object gas and a relative sensitivity.

Note that, as illustrated in FIG. 9, the relative sensitivity can be expressed by a linear function of A/F of the measurement-object gas, and therefore, in a case where a correction coefficient with which the relative sensitivity is equal to 100 is calculated for each value of A/F of the measurement-object gas, the relative sensitivity for A/F in a rich atmosphere needs to be calculated for one point in an experiment. Further, the correction coefficient for A/F may be calculated for each gas sensor 100, the average of the correction coefficients for a large number of gas sensors 100 may be used in all of the gas sensors 100, or the correction coefficient for a typical gas sensor 100 may be used in all of the gas sensors 100. Further, in FIG. 9, the horizontal axis represents A/F of the measurement-object gas; however, A/F of the measurement-object gas can be converted to the $O_2$ concentration of the measurement-object gas. Therefore, as illustrated in FIG. 10, the horizontal axis may represent the $O_2$ concentration of the measurement-object gas. Also in this case, the relative sensitivity can be approximated by a linear function of the $O_2$ concentration of the measurement-object gas, and a correction coefficient with which the relative sensitivity is equal to 100 can be calculated for each value of the $O_2$ concentration of the measurement-object gas.

According to this embodiment described above, when the measurement-object gas is in a rich atmosphere, the NOx concentration is corrected on the basis of A/F (or the $O_2$ concentration) of the measurement-object gas. Here, when the measurement-object gas is in a rich atmosphere, even if the actual concentration of NOx contained in the measurement-object gas remains the same, the sensor output decreases. Therefore, the accuracy of NOx measurement decreases. Accordingly, when the measurement-object gas is in a rich atmosphere, the NOx concentration is corrected on the basis of A/F (or the $O_2$ concentration) of the measurement-object gas. As a consequence, the accuracy of measurement of the concentration of NOx contained in the measurement-object gas in a rich atmosphere increases.

Further, the gas sensor 100 can detect A/F of the measurement-object gas. Therefore, the number of sensors can be made smaller than that in a case where the gas sensor 100 receives A/F detected by a sensor other than the gas sensor 100.

Further, a correction coefficient for each value of A/F (or the $O_2$ concentration) of the measurement-object gas when the measurement-object gas is in a rich atmosphere is stored in advance in the memory 94 of the control device 90, and the CPU 92 uses the correction coefficient corresponding to A/F to make a correction. Accordingly, the sensor output can be corrected with a high accuracy.

Other Embodiments

The present invention is not limited to the embodiments described above, and various modifications can be made without departing from the technical scope of the present invention, as a matter of course.

Figure 11:
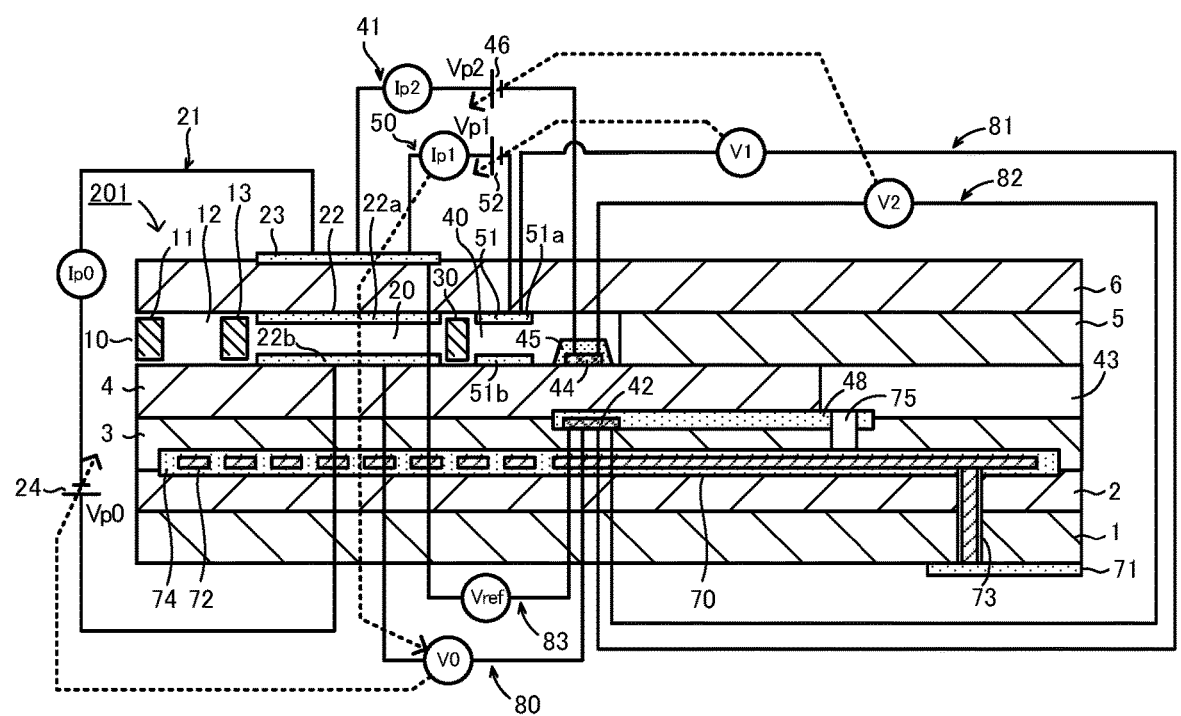
FIG. 11 is a schematic cross-sectional view of a sensor element 201 according to a modification.

For example, in the embodiments described above, the sensor element 101 of the gas sensor 100 includes the first internal cavity 20, the second internal cavity 40, and the third internal cavity 61; however, the sensor element 101 is not limited to this. For example, like a sensor element 201 illustrated in FIG. 11, the sensor element 101 need not include the third internal cavity 61. In the sensor element 201 according to a modification illustrated in FIG. 11, the gas inlet 10, the first diffusion control portion 11, the buffer space 12, the second diffusion control portion 13, the first internal cavity 20, the third diffusion control portion 30, and the second internal cavity 40 are formed adjacent to each other in this order so as to communicate with each other between the lower surface of the second solid electrolyte layer 6 and the upper surface of the first solid electrolyte layer 4. Further, the measurement electrode 44 is disposed on the upper surface of the first solid electrolyte layer 4 in the second internal cavity 40. The measurement electrode 44 is covered by a fourth diffusion control portion 45. The fourth diffusion control portion 45 is a film formed of a ceramic porous material, such as alumina ($Al_2O_3$). Further, similarly to the fourth diffusion control portion 60 of the embodiments described above, the fourth diffusion control portion 45 is responsible for limiting the amount of NOx that flows into the measurement electrode 44. The fourth diffusion control portion 45 also functions as a protective film for the measurement electrode 44. The ceiling electrode portion 51a of the auxiliary pump electrode 51 is formed so as to extend to a point right above the measurement electrode 44. The sensor element 201 thus configured can detect the NOx concentration by using the measurement pump cell 41 similarly to the embodiments described above. In this case, a space around the measurement electrode 44 functions as a measurement chamber. Note that the same constituent elements in FIG. 1 and FIG. 11 are assigned the same reference numeral.

The gas sensor 100 according to the embodiments described above can be used to measure the concentration of NOx and ammonia contained in an exhaust gas from an internal combustion engine. In this case, the internal combustion engine may be a gasoline engine or a diesel engine. The gasoline engine produces a rich atmosphere more frequently than the diesel engine does, and therefore, application of the present invention has greater significance for the gasoline engine.

In the embodiments described above, the gas sensor 100 detects A/F, and the detected A/F is used to correct the pump current Ip2 and the sensor output. However, the gas sensor 100 may receive a detection signal of A/F detected by a sensor other than the gas sensor 100 and use the A/F to correct the pump current Ip2 and the sensor output.

In the first and second embodiments described above, A/F of the measurement-object gas is used to correct the concentration of the NOx gas; however, the oxygen concentration may be used instead of A/F. A/F and the oxygen concentration of the measurement-object gas can be converted to each other, and therefore, A/F can be used to make a correction or the oxygen concentration can be used to make a correction.

In the first embodiment described above, expressions (1) and (2) are stored in the memory 94. However, instead of this, a map may be created on the basis of the graph in FIG. 3 and stored in the memory 94, and the NOx concentration corresponding to A/F and Ip2 may be obtained from the map. Further, in the second embodiment, expressions (3) and (4) are stored in the memory 94. However, instead of this, a map may be created on the basis of the graph in FIG. 6 and stored in the memory 94, and the ammonia concentration corresponding to A/F and Ip2 may be obtained from the map. Note that the map may be created for the NOx concentration or the ammonia concentration in 100 ppm increments, or the map may be created in increments of several tens ppm or several ppm. Further, instead of the map, a table may be used.

In the first embodiment described above, the correspondence between A/F and Ip2 in FIG. 3 is approximated by a linear function; however, the correspondence is not limited to this and can be approximated by a function (for example, a quadratic function) other than a linear function in some cases. In the second embodiment described above, the correspondence between A/F and Ip2 in FIG. 6 is approximated by a linear function; however, the correspondence is not limited to this and can be approximated by a function (for example, a quadratic function) other than a linear function in some cases.

In the third embodiment described above, the sensor output of the NOx concentration is corrected by using a correction coefficient calculated for each value of A/F of the measurement-object gas. With a method similar to this, the sensor output of the ammonia concentration may be corrected. Further, the pump current Ip2 may be corrected instead of the sensor output.

What is claimed is:

1. A gas sensor comprising:
   a layered body that has a plurality of stacked layers of an oxygen-ion-conductive solid electrolyte and in which a measurement-object gas flowing portion that allows a measurement-object gas containing a specific gas to be introduced thereinto and to flow therethrough is provided;
   a measurement electrode that is disposed in at least a part of an internal surrounding surface of a measurement chamber formed in the layered body and communicating with the measurement-object gas flowing portion;
   a controller configured to:
   detect a concentration of the specific gas on the basis of a measurement pump current that flows when oxygen is pumped out from the atmosphere around the measurement electrode in the measurement chamber so that an oxygen concentration in the measurement chamber becomes a predetermined low concentration, the oxygen that is pumped out being oxygen that is generated when the specific gas is reduced in the measurement chamber or being oxygen that is generated when a gas obtained as a result of conversion of the specific gas to an oxide is reduced in the measurement chamber where the specific gas is a non-oxide;
   detect an air-fuel ratio of an atmosphere of the measurement-object gas on the basis of a regulating pump current; and
   correct the measurement pump current on the basis of an oxygen concentration of the measurement-object gas in accordance with the detected air-fuel ratio upon determining that the measurement-object gas is in a rich atmosphere based on the detected air-fuel ratio being equal to or smaller than a stoichiometric air-fuel ratio,
   determine a corrected value of the concentration of the specific gas contained in an exhaust gas of an internal combustion engine as the measurement-object gas on the basis of the corrected measurement pump current, and
   output the corrected value as the sensor output.

2. The gas sensor according to claim 1, further comprising:
   an oxygen concentration regulating chamber that is provided on an upstream side of the measurement electrode in the measurement-object gas flowing portion;
   wherein the controller is further configured to detect an oxygen concentration of the measurement-object gas based on the regulating pump current that flows when oxygen is pumped out from or pumped into the oxygen concentration regulating chamber so that an oxygen concentration in the oxygen concentration regulating chamber matches a target concentration, wherein
   the controller is further configured to use the oxygen concentration of the measurement-object gas in the determination of the corrected value of the concentration of the specific gas.

3. The gas sensor according to claim 1, wherein as the oxygen concentration of the measurement-object gas, the air-fuel ratio of the measurement-object gas is used.

4. The gas sensor according to claim 1, further comprising a storage memory that stores a correspondence between the oxygen concentration of the measurement-object gas and a relative sensitivity of the measurement pump current or a correspondence between the oxygen concentration of the measurement-object gas and a relative sensitivity of the concentration of the specific gas when the measurement-object gas is in the rich atmosphere, wherein
   the controller is further configured to use the correspondence stored in the storage memory in the determination of the corrected value of the concentration of the specific gas.

5. The gas sensor according to claim 1, further comprising a storage memory that stores a correspondence between an actual concentration of the specific gas contained in the measurement-object gas, the oxygen concentration of the measurement-object gas, and the measurement pump current when the measurement-object gas is in the rich atmosphere, wherein the controller is further configured to use the correspondence stored in the storage memory in the determination of the corrected value of the concentration of the specific gas.

6. The gas sensor according to claim 5, wherein when the actual concentration of the specific gas contained in the measurement-object gas is represented by c [volume ppm], the air-fuel ratio is represented by R, and the measurement pump current is represented by Ip2 [ρA], the correspondence is expressed by Ip2=(p*c+q)*R+(r*c+s), where p, q, r, and s are constants used when c is within a predetermined low concentration range, or Ip2=(t*c+u)*R+(v*c+w), where t, u, v, and w are constants used when c exceeds the predetermined low concentration range.

* * * * *